United States Patent [19]

Hen

[11] Patent Number: 5,387,697
[45] Date of Patent: Feb. 7, 1995

[54] PROCESS FOR THE PREPARATION OF 1-[3-ACETYLTHIO-2(S)-METHYL-PROPANOYL]-L-PROLINE

[75] Inventor: Azucena C. Hen, Skillman, N.J.

[73] Assignee: Merck & Co., Inc., Rahway, N.J.

[21] Appl. No.: 260,271

[22] Filed: Jun. 13, 1994

[51] Int. Cl.$^6$ .................................... C07D 207/16
[52] U.S. Cl. ................................................ 548/533
[58] Field of Search .......................................... 548/533

[56] References Cited

U.S. PATENT DOCUMENTS

| | | | |
|---|---|---|---|
| 4,105,776 | 8/1978 | Ondetti et al. | 538/533 |
| 5,026,873 | 6/1991 | Anderson et al. | 548/533 |
| 5,166,361 | 11/1992 | Zepp | 548/533 |
| 5,276,207 | 1/1994 | Schneider et al. | 548/533 |

*Primary Examiner*—Joseph Paul Brust
*Attorney, Agent, or Firm*—Hesna J. Pfeiffer; Joseph F. DiPrima

[57] ABSTRACT

The intermediate 1-[3-acetylthio-2(s)-methyl-propanoyl]-1-proline is prepared by reacting L-proline with (R)-3-acetylthio-2-methyl propanoyl chloride at 0–5° C., with pH controlled at 7.5–8.5, using 2.5M potassium hydroxide and potassium phosphate buffer, which gives >97% pure material after crystallizing from the reaction mixture.

3 Claims, No Drawings

PROCESS FOR THE PREPARATION OF 1-[3-ACETYLTHIO-2(S)-METHYLPROPANOYL]-L-PROLINE

BACKGROUND OF THE INVENTION

Captopril, [the compound of the formula I]

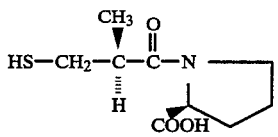

is an antihypertensive agent inhibiting the angiotensin converting enzyme (ACE). A high number of processes are known for the preparation of this compound. Several possibilities utilize L-proline, and acylate this with 3-mercapto protected-2-methylpropionic acid derivative.

According to one reaction route, the tert-butyl ester of L-proline is acylated with 3-acetylthio-2-methylpropionic acid in the presence of N,N'-dicyclohexylcarbodiimide, the product is transformed into its dicyclohexylamine salt and the latter is precipitated with acetonitrile and recrystallized from isopropanol. In this way dicyclohexylamine 1-[3-acetylthio-(2S)-methylpropionyl]-pyrrolidine-(2S)-carboxylate is obtained with a yield of 25%. The carboxylic acid is liberated with a yield of 83%. Then, the acetyl group protecting the mercapto group is removed by means of ammonia in methanol under a argon atmosphere with a yield of 74%. The compound of the formula I is separated as its dicyclohexylamine salt, from which the carboxylic acid is liberated with a yield of 75%. The starting tert-butyl ester of L-proline can be prepared from L-proline in 3 steps (i.e. N-benzyloxycarbonyl-L-proline, yield: 89%; tert-butyl ester of N-benzyloxycarbonyl-L-proline, yield: 93%; tert-butyl ester of L-proline, yield: 77%) and the acylating reagent, 3-acetylthio-2-methylpropionic acid can be prepared from methacrylic acid with thioacetic acid with a yield of 83%. Thus, the total synthesis consists of 8 reaction steps and the total yield is equivalent to 6.7% calculated for methacrylic acid and 8.1% calculated for L-proline, respectively.

According to a further reaction route, L-proline is directly acylated (e.g., following the Schotten and Baumann reaction) in the presence of an alkali hydroxide with 3-acetylthio-2-methylpropionyl chloride. The latter reagent is prepared from the corresponding carboxylic acid with a yield of 60%. Although the acylation step is performed with a yield of about 95%, the dicyclohexylamine 1-[3-acetylthio-(2S)-methyl-propionyl]-pyrrolidine-(2S)-carboxylate is obtained merely with a yield of 33%, and then follows the purification of the salt from isopropanol. Thus, the total yield of the whole Schotten-Baumann reaction is lower than 30%. The carboxylic acid is liberated from the dicyclohexylamine salt with a yield of 83%, then the acetyl group protecting the mercapto group is hydrolyzed by means of aqueous ammonia and the compound of the formula I is liberated on a column containing a cation exchanger with a yield of 42%. Although this reaction route consists of only 5 reaction steps, no improvement could be reached regarding the total yield being equivalent to 5.2% calculated for methacrylic acid, and 10.5%, calculated for L-proline, respectively.

Another problem with processes known in the prior art, such as U.S. Pat. No. 4,105,776, Example 152; or U.S. Pat. No. 5,026,873 (both to Squibb), is that a large amount of a dimeric by-product (15%) is prepared. This unwanted by-product has been identified as a S-acetylated product,

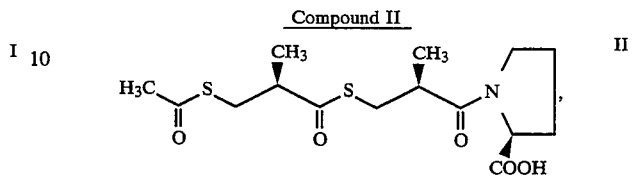

None of the known processes insures an economical method that could be performed simply and with an acceptable yield for the preparation of the compound of the formula I, while minimizing byproduct formation.

Therefore, it was the aim of the invention to eliminate the drawbacks connected with the known processes and to provide a process consisting of only a few reaction steps that can be performed economically on an industrial scale, and which does not result in unwanted by-product, thereby resulting in both high yield and high quality.

SUMMARY OF THE INVENTION

It has been found that the compound of the formula I can be prepared from L-proline in two reaction steps with a total yield of 67% through the acylation of L-proline, if L-proline is acylated with (R)-3-acetylthio-2-methylpropanoyl chloride of formula III:

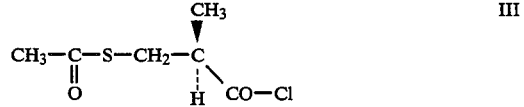

in the presence of KOH and potassium phosphate buffer at pH 7.5–8.5, and at a temperature of between about 0°–5° C. The resulting compound is 1-[3-acetylthio-2-(S)-methylpropanoyl]-L-proline,

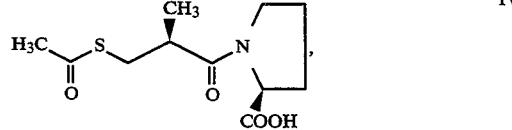

Compound IV, which also can be termed "S-acetyl captopril", can be acidified and then deblocked with sodium hydroxide to give captopril in yield of 67% relative to starting material of formula III, without any unwanted byproducts.

L-proline is acylated with the compound III above according to modified Schotten and Baumann preferably in aqueous medium at 0° to 5° C. in the presence of an alkali hydroxide and a phosphate buffer at pH 7.5–8.5. The alkali is employed in an amount corresponding to about 2.2 molar equivalent. Surprisingly, when the reaction mixture is acidified, the S-acetyl product is produced 82% yield, with >97% purity.

The alkali hydroxide is preferably KOH, employed in no more than 2.5M, in an amount about 2.2 molar equivalent.

The phosphate buffer is preferably potassium phosphate.

The invention is further described in the following examples.

EXAMPLE 1

Preparation of 1-[3-acetylthio-2-(S)methylpropanoyl)-L-Proline

A 0.25M potassium phosphate buffer, pH 8.4–8.5 solution (140 ml) is charged to a 500 ml 4-neck round bottom flask equipped with overhead agitator, thermocouple, pH meter, two addition funnels and nitrogen blanket. With the agitator on, 24.31 g of L-proline is charged to the flask at room temperature. The mixture is then cooled to 0°–5° C. 3-acetylthio-2-methylpropanoyl chloride (31.9 g) is then charged to the batch over a 4.0 hour period while controlling the batch temperature at 0°–5° C. and pH at 7.5–8.5. The 3-acetylthio-2-methylpropanoyl chloride addition causes exothermic reaction when added to the reaction mixture. The pH is controlled by dropwise addition of 2.5N potassium hydroxide.

At the end of the acid chloride addition, the batch is aged for 1.0 hour at 0°–5° C. and pH at 7.5–8.5; completion of the coupling reaction is monitored by HPLC.

The batch is then warmed to ambient temperature and concentrated HCl is added dropwise to pH 4.0 over 30 minutes. The batch is seeded and pH is further adjusted to 1.5 over 20 minutes using concentrated HCl. Heavy crystallization occurs during the pH adjustment to pH 1.5. The batch is then allowed to cool slowly over 1.0 hour to 0°–5° C. and filtered. The wet cake is washed with 2×40 ml of cold DI water and dried in vacuo at 40° C. to constant weight. The isolation yield = ~82% with >97 wt. % purity and <0.4 A % of the compound II impurity. Mother liquor loss = ~5%.

EXAMPLE 2

Use of Compound of Example 1 in Deblocking Step to make Captopril

Degassed DI water (47 ml) is charged to a 250 ml 4-neck round bottom flask equipped with overhead agitator, thermocouple, pH meter, addition funnel and nitrogen blanket. The flask is first purged 3 times with nitrogen and then kept as a nitrogen blanket, and oxygen rigorously excluded from the batch to avoid formation of disulfide.

With the agitator on, 16.20 g of S-acetyl-captopril is charged to the flask at ambient temperature. 50% sodium hydroxide (16.50 g) is added dropwise over 30 minutes to the slurry batch while controlling the temperature at ambient temperature with cooling water bath. The NaOH addition causes a 20°–25° C. exotherm when added to the batch if no cooling is provided, and the batch becomes homogenous at the end of the NaOH addition. The batch is then aged at ambient temperature for 45 minutes, completion of the deblocking operation being monitored by HPLC.

At the end of the 45 minutes age, concentrated HCl (~13 ml) is added slowly over 30 minutes to the batch to adjust the batch pH to 3.5 while controlling the batch temperature at 18°–20° C. The batch is then seeded at pH=3.5 and aged for 25 minutes at 18°–20° C.; heavy crystallization occurs during age at pH=3.5. The batch pH is then further adjusted to pH 1.5 by slow addition of concentrated HCl over 60 minutes.

The batch is then aged at room temperature for 30 minutes and is cooled slowly to 0°–5° C. over 1.0 hour. The batch is aged at 0°–5° C. for 1.0 hour and filtered. The product wet cake is washed with 1×15 ml of cold DI water and dried in vacuo at 50° C. to constant weight.

Isolation yield is ~80-82% and captopril purity of >99 wt % is obtained.

What is claimed is:

1. The process for the preparation of 1-[3-acetylthio-2(S)methylpropanoyl-L-proline which comprises reacting L-proline with approximately an equimolar amount of (R)-3-acetylthio-2-methyl propanoyl chloride at 0°–5° C., in the presence of 0.25M potassium phosphate buffer and enough 2.5M potassium hydroxide to keep the pH between 7.5–8.5; and then warming the reaction mixture to ambient temperature while adding conc. HCl to pH 1.5, and recovering the product thereby produced.

2. The process of claim 1 in which the reaction mixture is aged for about 1–2 hours at 0°–5° C. before warming to ambient.

3. The process of claims 1 or 2 in which the reaction mixture pH is first adjusted to 3.5–4.0 at 18°–20° C. by adding conc. HCl and aged for about 15 minutes to about 1 hour before the pH is dropped to 1.5 using additional conc. HCl.

* * * * *